(12) United States Patent
Davies et al.

(10) Patent No.: US 7,883,518 B1
(45) Date of Patent: Feb. 8, 2011

(54) SURGICAL KNOT

(75) Inventors: Kathleen H. Davies, Fremont, CA (US);
Zachary Warder-Gabaldon, Palo Alto, CA (US)

(73) Assignee: Cardica, Inc., Redwood City, CA (US)

( * ) Notice: Subject to any disclaimer, the term of this patent is extended or adjusted under 35 U.S.C. 154(b) by 1217 days.

(21) Appl. No.: 10/977,061

(22) Filed: Jan. 7, 2005

(51) Int. Cl.
*A61B 17/04* (2006.01)

(52) U.S. Cl. ...................................... 606/148

(58) Field of Classification Search ................. 606/139, 606/142, 148
See application file for complete search history.

(56) References Cited

U.S. PATENT DOCUMENTS

| | | | |
|---|---|---|---|
| 2,012,776 A | 8/1935 | Roeder | |
| 2,566,625 A * | 9/1951 | Nagelmann Clemens B | 606/147 |
| 3,090,386 A | 5/1963 | Curtis | |
| 3,177,021 A | 4/1965 | Benham | |
| 3,344,790 A | 10/1967 | Dorner | |
| 3,871,379 A | 3/1975 | Clarke | |
| 4,493,323 A | 1/1985 | Albright et al. | |
| 4,597,390 A | 7/1986 | Mulhollan et al. | |
| 4,614,187 A | 9/1986 | Mulhollan et al. | |
| 4,621,638 A * | 11/1986 | Silvestrini | 606/230 |
| 4,760,848 A | 8/1988 | Hasson | |
| 4,945,920 A | 8/1990 | Clossick | |
| 5,015,250 A | 5/1991 | Foster | |
| 5,037,433 A | 8/1991 | Wilk et al. | |
| 5,080,664 A * | 1/1992 | Jain | 606/148 |
| 5,129,912 A | 7/1992 | Noda et al. | |
| 5,147,373 A | 9/1992 | Ferzli | |
| 5,273,545 A | 12/1993 | Hunt et al. | |
| 5,275,611 A | 1/1994 | Behl | |
| 5,279,067 A | 1/1994 | Tollison | |
| 5,312,360 A | 5/1994 | Behl | |
| 5,320,629 A | 6/1994 | Noda et al. | |
| 5,405,352 A | 4/1995 | Weston | |
| 5,573,286 A | 11/1996 | Rogozinski | |
| 5,591,177 A | 1/1997 | Lehrer | 606/139 |
| 5,643,293 A | 7/1997 | Kogasaka et al. | 606/148 |
| 5,728,109 A * | 3/1998 | Schulze et al. | 606/139 |
| 6,712,831 B1 * | 3/2004 | Kaplan et al. | 606/153 |

OTHER PUBLICATIONS

Graumont, Raoul and Hensel, John. Encyclopedia of Knots and Fancy Rope Work, Fourth Edition (1958), Preface, pp. 11, 56, 72, 74, 76, 78, 82, 84, 86, 89, 92, 95, 97, 99, 102, 105; plates 30-49.

* cited by examiner

*Primary Examiner*—(Jackie) Tan-Uyen T Ho
*Assistant Examiner*—Melanie Tyson
(74) *Attorney, Agent, or Firm*—Brian A. Schar

(57) ABSTRACT

A length of suture is provided, and a knot is partially tied in that suture around a tube. The partially-tied knot includes a noose portion connected to a loosely-tied barrel portion. The knot is tied by holding a standing end of the suture substantially stationary and pulling the running end of the suture through the noose. The knot locks upon tightening, making it suitable for surgical applications.

8 Claims, 4 Drawing Sheets

US 7,883,518 B1

SURGICAL KNOT

FIELD OF THE INVENTION

The present invention relates generally to knots, and more particularly to a surgical knot and a method for tying it.

BACKGROUND

Anastomosis is a procedure where two separate tubular or hollow organs are surgically grafted together to form a continuous fluid channel between them. A vascular anastomosis is performed between blood vessels to create or restore blood flow. When a patient suffers from coronary artery disease (CAD), an occlusion or stenosis in a coronary artery restricts blood flow to the heart muscle. In order to treat CAD, the area where the occlusion occurs is bypassed to reroute blood flow by grafting a vessel in the form of a harvested artery or vein, or a prosthesis. Anastomosis is performed between a graft vessel and a target vessel in order to bypass the blocked coronary artery, circumvent the occlusion and restore adequate blood flow to the heart muscle. This treatment is known as a coronary artery bypass graft procedure (CABG).

An anastomosis may be compliant or noncompliant. A noncompliant anastomosis is one in which the target vessel is not substantially free to expand or contract circumferentially and longitudinally in proximity to the anastomosis site. A compliant anastomosis is one in which the target vessel is substantially free to expand or contract circumferentially and longitudinally in proximity to the anastomosis site. A traditional sutured anastomosis is compliant, and for this reason some surgeons may prefer to utilize an anastomosis system that provides a compliant anastomosis, particularly between a graft vessel and the aorta or other source of arterial blood.

SUMMARY

In one aspect of the invention, a length of suture is provided, and a knot is partially tied in that suture around a tube. Part of the suture extends into the lumen of the tube, and the running end of the suture extends out of an end of the lumen. The tube facilitates formation of a partially-tied knot, and may hold the partially-tied knot in place prior to its use.

In another aspect of the invention, the partially-tied knot includes a noose connected to a barrel. The barrel of the partially-tied knot may be an overhand knot loosely formed around the tube. Alternately, the barrel portion is a different type of knot. The barrel may be spaced apart from an end of the tube. The noose of the partially-tied knot is a length of suture extending out of an end of the lumen of the tube that connects to the barrel portion, thereby forming a loop.

In another aspect of the invention, the radius of each curve in the barrel portion of the partially-tied knot may be greater than or equal to twice the diameter of the suture. This curvature prevents breakage of the suture during tying, and also promotes proper formation of the knot.

In another aspect of the invention, the knot is tied by holding a standing end or other portion of the suture substantially stationary and pulling the running end of the suture through the noose. Advantageously, the running end is pulled relatively fast to tie the knot, such as at a speed of substantially 0.4 inches per second. The knot locks upon tightening, making it suitable for surgical applications.

BRIEF DESCRIPTION OF THE DRAWINGS

The use of the same reference symbols in different figures indicates similar or identical items.

DETAILED DESCRIPTION

Figure 1:
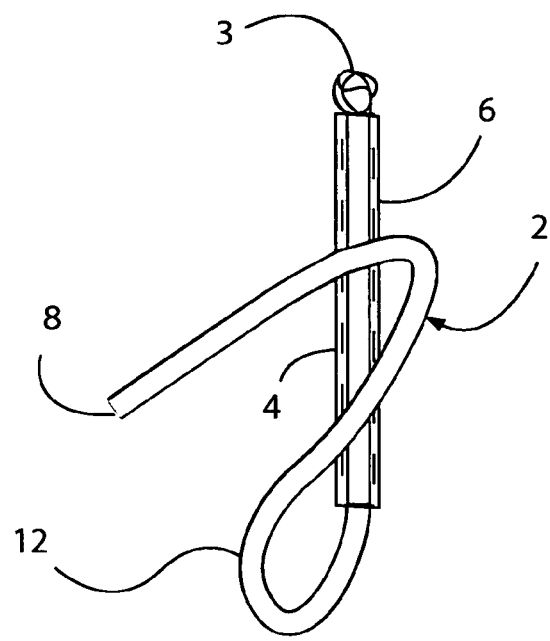
FIG. 1 is a front view of the first step in making a partially-tied knot in a length of suture.

Referring to FIG. 1, a tube 4 has a lumen 6 extending from one end along at least part of its length. A length of suture 2 extends from the lumen 6 out of an end of the tube 4. One end of the suture 2 may be anchored or otherwise fixed relative to the tube 4, such that that end of the suture 2 remains substantially stationary relative to the tube 4. That end of the suture 2 is referred to as the standing end 3 of the suture 2. The standing end of the suture 2 may be fixed directly to the tube 4. For example, the standing end 3 of the suture 2 may be knotted or otherwise configured such that the standing end 3 has a larger diameter than that of the lumen 6 of the tube 4. That knotted standing end 3 may be affixed to the tube 4, such as by adhesive. However, the knotted standing end 3 instead may be free relative to the tube 4, such that the knot prevents distal but not proximal motion of the standing end 3 of the suture 2. Alternately, a different part of the suture 2 than the standing end 3 may be connected to the tube 4. Alternately, the suture 2 may extend completely through the tube 4 and be anchored, fixed or otherwise connected to a structure other than the tube 4. For example, the suture 2 may extend completely through the lumen 6 to a structure or mechanism positioned away from the tube 4 to which the suture 2 is attached.

The end of the suture 2 opposite the standing end 3 may be referred to as the running end 8 of the suture 2. The suture 2 may be polypropylene suture, size 4-0 or 5-0. Alternately, the suture 2 may be fashioned from a different material, such as an absorbable material. Alternately, the suture 2 may be a larger or a smaller size.

The tube 4 may be part of a larger tool (not shown) used for performing anastomosis. Such a tool for performing anastomosis may include a number of separate tubes 4, where a corresponding suture 2 extends from each tube 4, such that a number of separate and independent knots can be tied substantially simultaneously during an anastomosis procedure. Similarly, the tube 4 may be part of a larger tool used for performing any suitable surgical procedure, such as but not limited to closure of a puncture in a patient's femoral artery. Alternately, the tube 4 may be a mandrel or other structure that is used merely to form a partially-tied knot such as described below, then removed. Alternately, the tube 4 is not used at all, and the partially-tied knot is otherwise formed such as described below.

Initially, a knot is partially tied in the length of suture 2 extending from an end of the tube 4. Referring to FIG. 1, the running end 8 of the suture 2 is laid atop the outer surface of the tube 4. The suture 2 is manipulated to form a noose 12 that curves outward from the tube 4. That is, at least part of the noose 12 of is spaced apart from the tube 4, rather than tightened down onto the tube 4. Part of the noose 12 may extend distal to the tube 4 as well.

Figure 2:
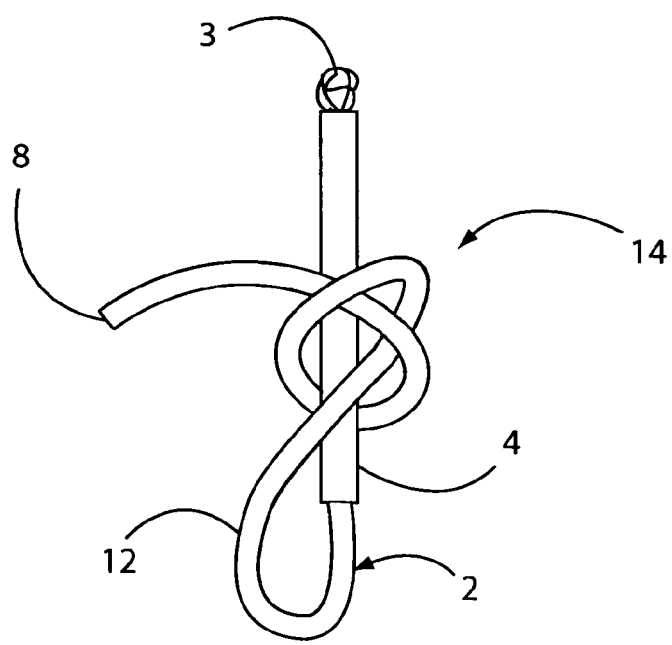
FIG. 2 is a front view of the final step in making a partially-tied knot in a length of suture, resulting in a partially-tied knot.

Referring to FIG. 2, the suture 2 has been manipulated further to form a loose overhand knot 14 around the tube 4. The overhand knot 14 may be referred to as the barrel 14. Where the barrel 14 is an overhand knot, the barrel 14 includes a single winding of suture 2. Alternately, the barrel 14 includes two or more windings of suture 2. Alternately, a knot other than an overhand knot forms the barrel 14. The barrel 14 is connected to the noose 12, and may be positioned proximal to the noose 12. The overhand knot 14 is loosely formed around the tube 4, forming a pretzel-like shape. Advantageously, the radius of all curves in the overhand knot 14 is substantially greater than or equal to twice the diameter of the suture 2. Such curvature may be important when tying the knot, as described below. The barrel 14 may be spaced apart from an end of the tube 4.

Figure 3:
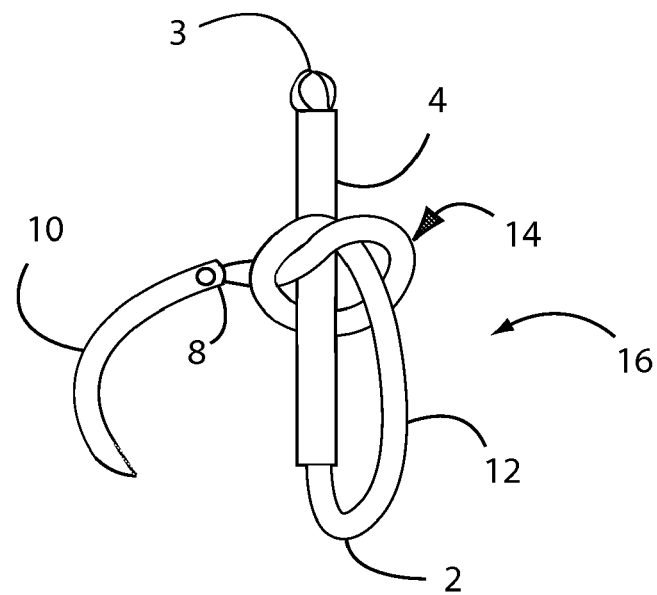
FIG. 3 is a front view of the partially-tied knot of FIG. 2, showing a needle attached to the running end of the suture.

Referring also to FIG. 3, after the overhand knot 14 has been loosely formed, a partially-tied knot 16 has been formed, having a noose 12 and a barrel 14. The noose 12 and the barrel 14 are different regions of the same suture 2. Alternately, the noose 12 and the barrel 14 may be formed from different lengths of suture that are connected together in any suitable manner. In the partially-tied knot, at least part of the suture 2 that forms the noose 12 remains spaced apart from the tube 4. The running end 8 of the suture and the noose 12 may be on opposite sides of the barrel 14, physically and/or topologically.

A needle 10 may be connected to the running end 8 of the suture 2. This connection may be accomplished in any suitable manner. Alternately, the running end 8 of the suture 2 may be connected to a post, clip or other structure (not shown). Alternately, the running end 8 of the suture 2 may be unconnected to a needle 10 or other structure. Alternately, the needle 10 may be separable from the running end 8 of the suture 2. Alternately, the needle may be connected to a part of the suture 2 other than the running end 8.

Figure 4:
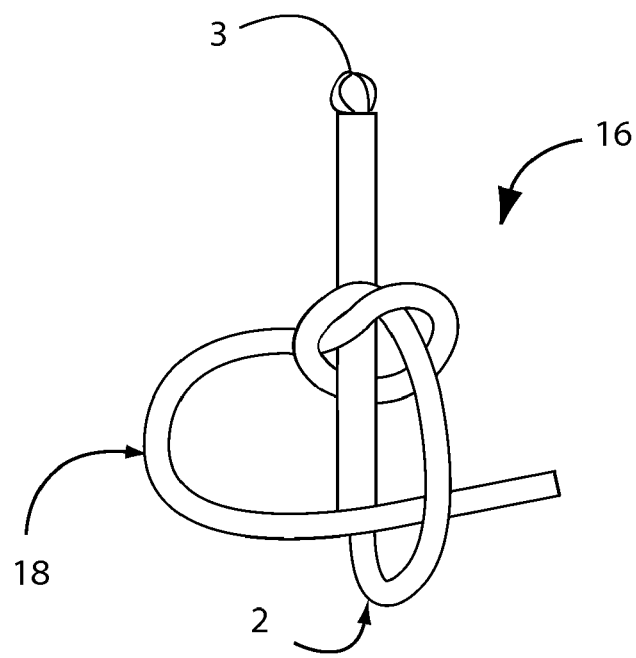
FIG. 4 is a front view of the first step in fully tying the partially-tied knot of FIGS. 2-3.

Referring also to FIG. 4, to tie the partially-tied knot 16, the needle 10 is passed through the noose 12 of the partially-tied knot 16. That is, the needle 10 is passed between the tube 4 and the portion of the suture 2 forming the noose 12 of the suture 2. Alternately, if the needle 10 is not used, the running end 8 of the suture 2 and/or any structure attached to the running end 8 of the suture 2 is passed through the noose 12. As the needle 10 and the running end 8 of the suture 2 are moved, the standing end 3 of the suture 2 is held substantially stationary. In the course of moving the needle 10 through the noose 12, a lobe 18 is formed between the barrel 14 and the noose 12. The needle 10 may be moved by hand or by a mechanism operatively connected to the needle 10. For example, where the tube 4 is part of a larger tool used for performing a surgical procedure such as anastomosis, that larger tool may be configured to move the needle 10.

Figure 5:
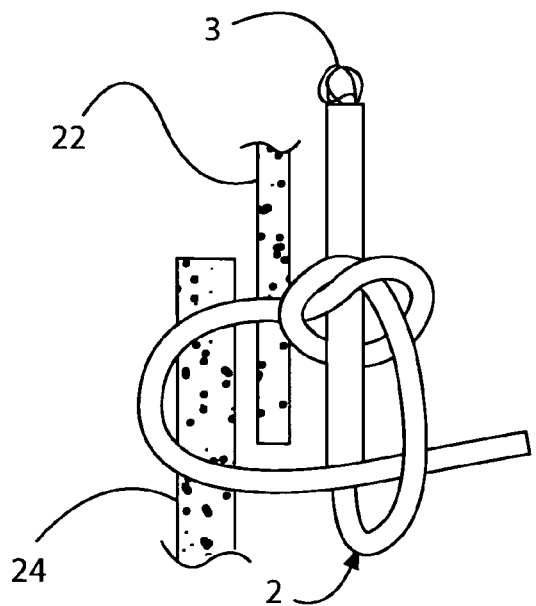
FIG. 5 is a front view of the first step shown in FIG. 4, where the tying process is performed in the context of an end-to-side anastomosis.

Referring also to FIG. 5, where the partially-tied knot 16 is to be used to perform an end-to-side anastomosis, tissue at the end of a first vessel 22 may be curved or everted onto a side of the tube 4, and the running end 8 of the suture 2 is moved through that tissue. The side of a second vessel 24 may be positioned in proximity to or in contact with the tissue at the end of the first vessel 22, and the running end 8 of the suture 2 is moved through that tissue as well. Next, the needle 10 is moved through the noose 12, as described above. The running end 8 of the suture 2 may pass through the tissue of the first vessel 22 and/or the second vessel 24 a second time, at a location spaced apart from the location of its first pass through that tissue, prior to entering the noose 12. Alternately, the needle 10 may not pass through tissue a second time prior to entering the noose 12. Alternately, the suture 2 may be moved through the tissue of the vessels 22, 24 in a different manner and/or in a different arrangement or topology.

The suture 2 continues to be pulled through the noose 12. Advantageously, the suture 2 is pulled through the noose 12 relatively quickly. For example, the suture 2 may be pulled at a rate of approximately 0.4 inches per second, which has been determined experimentally to be advantageous. The looseness of the barrel 14 is important as the suture 2 is pulled through the noose 12. If the radius of all curves in the overhand knot 14 is substantially greater than or equal to twice the diameter of the suture 2, then the partially-tied knot 16 can be tied smoothly. However, if the overhand knot 14 is formed more tightly, the likelihood that the partially-tied knot 16 will lock up and bind onto the tube 4 increases, such that the partially-tied knot 16 will not be tied properly.

As the suture 2 continues to pass through the noose 12, the length of the lobe 18 decreases. This decrease in the length of the lobe 18 is limited by the thickness and compliance of tissue 22, 24 that is engaged by the lobe 18. However, when the lobe 18 has reached a final length, tension still may be applied to the suture 2. Because the standing end 3 of the suture 2 is substantially stationary, the decreasing length of the lobe 18 pulls the barrel 14 toward the end of the tube 4.

Figure 6:
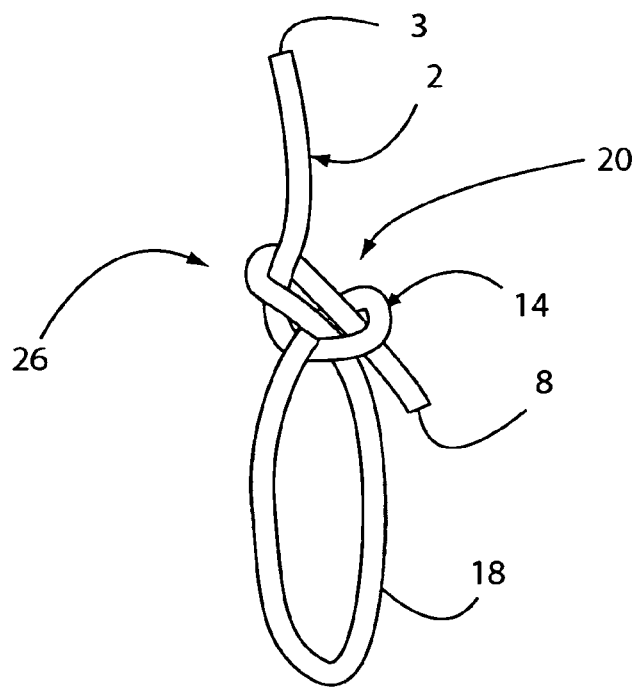
FIG. 6 is a front view of a fully-tied knot, shown slightly loose for clarity.

Referring also to FIG. 6, after the running end 8 of the suture 2 has been pulled through the noose 12 and the lobe 18 has reached a final length, the noose 12 is pulled through the barrel 14, such as by motion of the standing end 3 and/or the tube 4. For clarity, tissue 22, 24 and the needle 10 are not shown. The noose 12 pulls a portion 26 of the suture 2 in proximity to the running end 8 through the barrel 14, forming a loop 26. The noose 12 may pull the portion 26 of the suture 2 into and/or through the barrel 14 before or during tightening of the barrel 14 that results from application of tension to the suture 2. The noose 12 itself may vanish after it pulls the portion of the suture 2 in proximity to the running end 8 through the barrel 14. In addition, the conversion to a fully-tied knot 20 may result in the barrel 14 rotating relative to the lobe 18. By pulling the noose 12 and a portion of the suture 2 in proximity to the running end 8 through the barrel 14, and tightening the barrel 14, the partially-tied knot 16 is converted to a fully-tied knot 20 that is locked into position.

Figure 7:
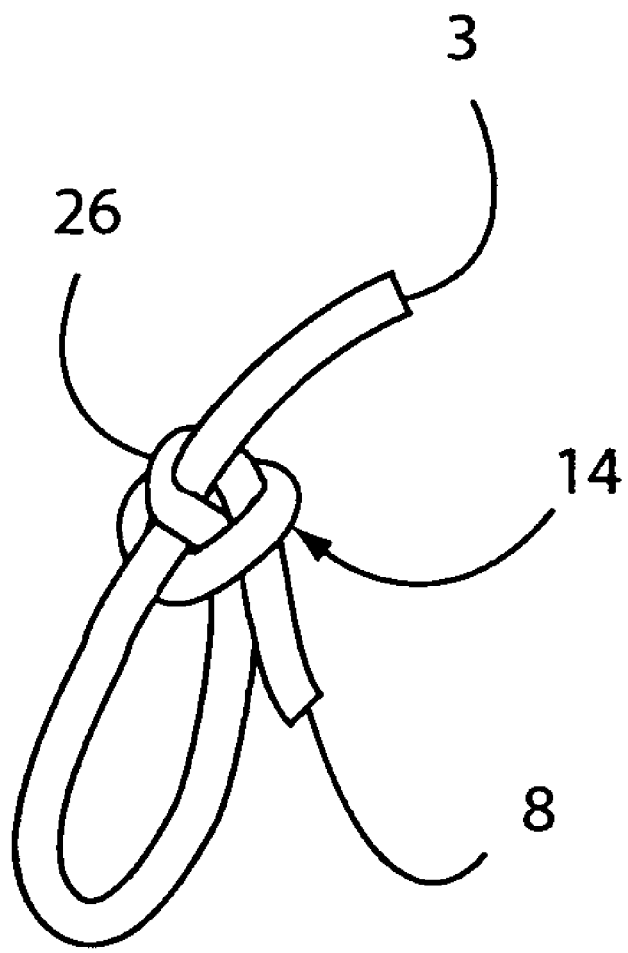
FIG. 7 is a front view of the tied knot of FIG. 6, shown fully-tied.

FIG. 7 illustrates the locked nature of the fully-tied knot 20. For clarity, the tube 4 is not shown. The barrel 14 cinches down onto the loop 26, which in turn is wrapped around a length of suture 2 extending toward the standing end 3. The size of the loop 26 is too large to allow it to pass out of the cinched-down barrel 14, such that the barrel 14 locks the loop 26 and thus the knot 20 in position. Where the barrel 14 is an overhand knot, for example, the barrel 14 includes a single winding of suture 2, and the noose 12 and a portion of the suture 2 in proximity to the running end 8 are pulled through that single winding and locked into position.

The barrel 14 then moves off the end of the tube 4. The suture 2 may be cut between the knot 20 and the standing end 3 of the suture 2 in order to release the knot 20 from the remainder of the suture 2. Alternately, the standing end 3 of the suture 2 may be released from the lumen of the tube 4, released from a separate mechanism proximal to or otherwise positioned relative to the tube 4, or otherwise separated from the tube 4, in order to free the knot 20. The knot 20 is substantially locked, meaning that it does not substantially loosen in use. Thus, the knot 20 is particularly suitable for surgical applications within the human body, such as in the thoracic cavity.

While the invention has been described in detail, it will be apparent to one skilled in the art that various changes and modifications can be made and equivalents employed, without departing from the present invention. It is to be understood that the invention is not limited to the details of construction, the arrangements of components and/or the details of operation set forth in the above description or illustrated in the drawings. Headings and subheadings are for the convenience of the reader only. They should not and cannot be construed to have any substantive significance, meaning or interpretation, and should not and cannot be deemed to be limiting in any way, or indicate that all of the information relating to any particular topic is to be found under or limited to any particular heading or subheading. The contents of each section of this document are merely exemplary and do not limit the scope of the invention or the interpretation of the claims. Therefore, the invention is not to be restricted or limited except in accordance with the following claims and their legal equivalents.

What is claimed is:

1. A method of suturing an end of a first vessel to the side of a second vessel, comprising:

providing a length of suture having a standing end and a running end, and a tube having a lumen at least partially therein, wherein said suture extends longitudinally through the entire said lumen of said tube and out of an end of said tube;

connecting a needle to said running end;

forming a portion of said suture into a loosely-formed overhand knot around said tube, said overhand knot having only a single winding of suture;

leaving a portion of said suture spaced apart from said tube to form a noose connected to said loosely-formed overhand knot;

placing an end of the first vessel in proximity to said tube;

passing said needle through at least one location in proximity to the end of the first vessel and at least one location on the side of the second vessel; and pulling said running end through said noose portion, resulting in a fully-tied knot.

2. The method of claim 1, further comprising passing said needle through at least one of the first vessel and the second vessel a second time.

3. The method of claim 1, wherein said pulling is performed at a rate of substantially 0.4 inches per second.

4. The method of claim 1, wherein said suture is polypropylene suture.

5. The method of claim 1, wherein said suture is substantially size 4-0.

6. The method of claim 1, wherein said suture is substantially size 5-0.

7. The method of claim 1, further comprising holding said standing end of said suture substantially stationary during said pulling.

8. The method of claim 1, further comprising pulling said fully-tied knot off of said tube.

* * * * *